United States Patent [19]

Gorys et al.

[11] Patent Number: 5,552,405

[45] Date of Patent: Sep. 3, 1996

[54] SUBSTITUTED PYRROLIDINE DERIVATIVES AS HIV PROTEASE INHIBITORS

[75] Inventors: Vida Gorys, Dollard des Ormeaux; François Soucy, Lachenaie; Christiane Yoakim, Laval; Pierre L. Beaulieu, Montréal, all of Canada

[73] Assignee: Bio-Mega/Boehringer Ingelheim Research, Inc., Laval, Canada

[21] Appl. No.: 509,268

[22] Filed: Jul. 31, 1995

Related U.S. Application Data

[63] Continuation of Ser. No. 326,442, Oct. 20, 1994, abandoned, which is a continuation of Ser. No. 198,237, Feb. 18, 1994, abandoned, which is a continuation of Ser. No. 25,681, Mar. 3, 1993, abandoned, which is a continuation of Ser. No. 850,596, Mar. 13, 1992, abandoned.

[51] Int. Cl.$^6$ .................... A61K 31/40; C07D 207/09
[52] U.S. Cl. .................... 514/269; 514/314; 514/343; 514/423; 514/319; 546/169; 546/278.4; 546/256; 546/279.1; 546/269.7; 548/537
[58] Field of Search .................... 514/269, 314, 514/343, 423; 544/319; 546/281; 548/537

[56] References Cited

FOREIGN PATENT DOCUMENTS 346847  12/1989  European Pat. Off. ...... C07D 207/16

*Primary Examiner*—Jacqueline Haley
*Attorney, Agent, or Firm*—Robert P. Raymond; Alan R. Stempel; Mary-Ellen M. Devlin

[57] ABSTRACT

Disclosed herein are compounds of formula 1

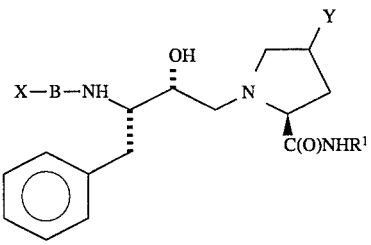

wherein X is a terminal group, for example, an aryloxycarbonyl or an alkanoyl; B is absent or an amino acid residue, for example, Val or Asn; $R^1$ is alkyl; and Y is a ring substituent, for example, benzyl, benzyloxy, phenylthio or 2-pyridinylthio. The compounds inhibit the activity of human immunodeficiency virus (HIV) protease and interfere with HIV induced cytopathogenic effects in human cells. These properties render the compounds useful for combating HIV infections.

3 Claims, No Drawings

SUBSTITUTED PYRROLIDINE DERIVATIVES AS HIV PROTEASE INHIBITORS

This is a continuation of application Ser. No. 326,442, filed Oct. 20, 1994, now abandoned, which is a continuation of application Ser. No. 198,237, filed Feb. 18, 1994, now abandoned, which is a continuation of application Ser. No. 025,681, filed Mar. 3, 1993, now abandoned, which is a continuation of application Ser. No. 850,596, filed Mar. 13, 1992, now abandoned.

FIELD OF INVENTION

This invention relates to compounds exhibiting activity against particular retroviruses, to processes for producing the compounds, to pharmaceutical preparations thereof, and to a method of using the compounds to combat infections caused by the retroviruses.

BACKGROUND OF THE INVENTION

In 1983, a retrovirus, known as human immunodeficiency virus type 1 (HIV-1), was established as a causative agent of acquired immune deficiency syndrome (AIDS), see R. C. Gallo and L. Montagnier, Scientific American, 259(4), 40 (1988). This virus has become a pestilence of alarming proportion. More recently, the closely related virus, human immunodificiency virus type 2 (HIV-2) has been identified as a second causative agent of AIDS.

The identification of human immunodeficiency virus (HIV) as a causative agent and the development of methods to grow the virus in quantity have resulted in the discovery of compounds which inhibit the replication of HIV in vitro. The most important class of inhibitor compounds identified in this manner is a group of dideoxynucleosides of which 3'-azido-3'-deoxythymidine (known also a zidovudine or AZT) and, more recently, 2',3'-dideoxyinosine (known also as didanosine or DDI) are used therapeutically to manage certain patients with symptomatic HIV infections. This class of compounds has been found to interfere with the life cycle of HIV by inhibiting reverse transcriptase. This enzyme converts viral RNA to double-stranded deoxyribonucleic acid (DNA) and as such is an essential enzyme for HIV replication. In addition to inhibiting reverse transcriptase, other stages of the HIV life cycle have been identified as targets for developing anti-AIDS drugs. One target that is receiving increased attention is an HIV-encoded enzyme known as HIV protease. This enzyme, like the reverse transcriptase, is encoded by the pol gene and is essential for HIV growth. It is responsible for effecting certain cleavages within the gag (p55) or gag-pol (p180) proteins to release structural proteins, e.g. p17 and p24, and enzymes, including itself, found in mature infectious virions. Thus, inhibitors of HIV protease can block the HIV life cycle.

The increased attention given to HIV protease over the last few years is reflected in the increase in reports of the discovery of agents which block the enzyme. See, for example, the recent review on protease inhibitors by D. W. Norbeck and D. J. Kempf, Annual Reports In Medicinal Chemistry, 26, 141 (1991). As noted in the latter review and reported by D. H. Rich et al., J. Med. Chem., 33, 1285 (1990) and N. A. Roberts et al., Science, 248, 358 (1990), two potent series of HIV protease inhibitors have been realized by the placement of a hydroxyethylamine transition state analog (TSA) in a peptide having the p17/p24 substrate cleavage site sequence. Biological investigations of lead compounds of the Roberts et al. series have been reported by H. A. Overton et al., Virology, 179, 508 (1990), J. A. Martin et al., Biochem. Biophys. Res. Commun., 176, 180 (1991) and. J. C. Craig et al., Antiviral Chemistry and Chemotheraphy, 2, 181 (1991).

Other disclosures of HIV protease inhibitors having a hydroxyethylamine TSA include:
B. K. Handa et al., European patent application 346 847, published Dec. 20, 1989,
G. B. Dreyer et al., European patent application 352 000, published Jan. 24, 1990,
D. J. Kempf et al., European patent application 402 646, published Dec. 19, 1990, and
K. E. B. Parkes et al., Canadian patent application 2,030, 415, published Jun. 12, 1991,
J. A. Martin and S. Redshaw, European patent application 432 695, published Jun. 19, 1991.

The present application discloses substituted pyrrolidine derivatives having an ethylamine TSA incorporated in their structure. The derivatives are potent inhibitors of HIV protease. Moreover, a capacity to inhibit HIV induced cytopathogenic effects in human cells has been demonstrated for the compounds. Such properties, together with the attributes of a relatively selective action and an apparent lack of toxicity, renders the compounds useful as agents for combating HIV infections.

SUMMARY OF THE INVENTION

The compounds of this invention are represented by formula 1

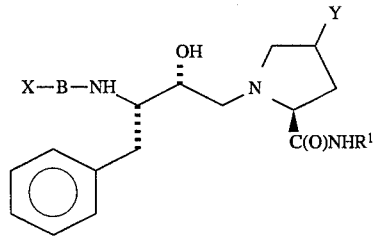

wherein
X is $R^2OC(O)$, $R^2C(O)$ or $R^2NR^3C(O)$ wherein $R^2$ is
(i) lower alkyl,
(ii) lower cycloalkyl,
(iii) phenyl or phenyl monosubstituted with halo, hydroxy, lower alkyl or lower alkoxy,
(iv) phenyl(lower)alkyl or phenyl(lower)alkyl wherein the aromatic portion thereof is monosubstituted with halo, hydroxy, lower alkyl or lower alkoxy,
(v) 1-naphthyl or 2-naphthyl,
(vi) (Her) or (Het)-(lower alkyl) wherein Het represents a five or six membered, monovalent heterocyclic radical containing one or two hetero-atoms selected from nitrogen, oxygen and sulfur, or
(vii) 2-quinolinyl or 3-quinolinyl, and
$R^3$ is hydrogen or lower alkyl; or X is $R^{2A}OCH_2C(O)$ wherein $R^{2A}$ is phenyl or phenyl monosubstituted, disubstituted or trisubstituted with lower alkyl or halo;

B is absent or the divalent radical $—NHCHR^4C(O)—$ wherein $R^4$ is lower alkyl; lower cycloalkyl; (lower cycloalkyl)-(lower alkyl); phenylmethyl; or lower alkyl monosubstituted with hydroxy, carboxy, lower alkoxycarbonyl, aminocarbonyl, (lower alkyl)aminocarbonyl or di(lower alkyl)aminocarbonyl;

$R^1$ is lower alkyl or lower cycloalkyl;

Y is lower alkyl; lower cycloalkyl; phenyl or phenyl monosubstituted with halo, hydroxy, lower alkyl or lower alkoxy; phenylmethyl or phenylmethyl monosubstitued with halo, hydroxy, lower alkyl or lower alkoxy; or Y is $W(CH_2)_nZ$ wherein W is oxo, thio, sulfinyl or sulfonyl, Z is lower alkyl; phenyl or phenyl monosubstituted with halo, hydroxy, lower alkyl or lower alkoxy; or (Het) wherein (Het) is as defined hereinbefore; and n is zero or one; or a therapeutically acceptable acid addition salt thereof.

It is to be understood that the term "B is absent", used herein with reference to formula 1, means that the symbol B has become a covalent bond joining "X" to the secondary amino group which otherwise would be joined to "B".

A preferred group of compounds of the invention is represented by formula 1 wherein X is $R^2OC(O)$ or $R^2C(O)$ wherein $R^2$ is lower alkyl; phenyl(lower)alkyl; phenyl(lower)alkyl wherein position 4 of the phenyl portion is substituted with chloro, fluoro, hydroxy, methyl or methoxy; 1-naphthyl; 2-naphthyl; 2-furyl; 2-thienyl; 2-pyridinyl; 4-pyridinyl; 2-pyridinylmethyl; 4-thiazolylmethyl or 2-quinolinyl; or X is $R^{2A}OCH_2C(O)$ wherein $R^{2A}$ is phenyl or phenyl mono-, di- or trisubstituted with lower alkyl or halo at a position or positions selected from the group consisting of positions 2, 4 and 6;

B is absent or the divalent radical —$NHCHR^4C(O)$— wherein $R^4$ is lower alkyl, or lower alkyl monosubsituted with hydroxy, lower alkoxycarbonyl, aminocarbonyl, (lower alkyl)aminocarbonyl or di(lower alkyl)aminocarbonyl;

$R^1$ is 1-methylethyl, 1,1-dimethylethyl, 2-methylpropyl, cyclopropyl, cyclobutyl, cyclopentyl or cyclohexyl;

Y is lower cycloalkyl, phenyl, 4-chlorophenyl, 4-bromophenyl, 4-fluorophenyl, 4-methylphenyl, 4-methoxyphenyl, phenylmethyl, (4-fluorophenyl)methyl or (4-methylphenyl)methyl; or Y is $W(CH_2)_nZ$ wherein W and n are as defined hereinabove and Z is lower alkyl, phenyl, 2-furyl, 2-thienyl, 2-pyridinyl, 3-pyridinyl, 4-pyridinyl, 4-thiazolyl, 2-pyrimidinyl, 4,6-dimethyl-2-pyrimidinyl or 2,6-dimethyl-4-pyrimidinyl; or a therapeutically acceptable acid addition salt thereof.

A more preferred group of compounds represented by formula 1 in which X is tert-butyloxycarbonyl, benzyloxycarbonyl, (4-chlorophenyl)methoxycarbonyl, (4-hydroxyphenyl)methoxycarbonyl, (4-methoxyphenyl)methoxycarbonyl, acetyl, benzoyl, 1-naphthalenylcarbonyl, 2-naphthalenylcarbonyl, 2-pyridinylmethoxycarbonyl, 2-quinolinylcarbonyl, phenoxyacetyl, (2-methylphenoxy) acetyl, (2,4-dimethylphenoxy)acetyl, (2,6-dimethylphenoxy)acetyl. (2,4,6-trimethylphenoxy)acetyl, (4-chlorophenoxy)acetyl or (4-fluoro-2,6-dimethylphenoxy)acetyl;

B is absent or the divalent radical —$NHCHR^4C(O)$— wherein $R^4$ is 1-methylethyl, 1,1-dimethylethyl, 1-methylpropyl, 2-methylpropyl, methoxycarbonylmethyl, ethoxycarbonylmethyl or aminocarbonylmethyl;

$R^1$ is 1,1-dimethylethyl or cyclopropyl;

Y is cyclohexyl, phenyl, 4-chlorophenyl, 4-fluorophenyl, 4-methoxyphenyl, benzyl, (4-methoxyphenyl)methyl, 2-methylpropoxy, phenoxy, 2-pyridinyloxy, 3-pyridinyloxy, 4-pyridinyloxy, 2-pyrimidinyloxy, 4,6-dimethyl-2-pyrimidinyloxy, 2,6-dimethyl-4-pyrimidinyloxy, benzyloxy, 2-pyridinylmethoxy, 4-thiazolylmethoxy, 2-pyrimidinylmethoxy, phenylthio, phenylsulfinyl, phenylsulfonyl, 2-pyridinylthio, 3-pyridinylthio, 4-pyridinylthio, 2-pyrimidinylthio, 4,6-dimethyl-2-pyrimidinylthio, benzylthio, benzylsulfinyl, benzylsulfonyl, (2-pyridinylmethyl)thio, (3-pyridinylmethyl)thio or (4-pyridinylmethyl)thio; or a therapeutically acceptable acid addition salt thereof.

A most preferred group of the compounds is represented by formula 1 in which X is tert-butyloxycarbonyl, benzyloxycarbonyl, acetyl, 2naphthalenylcarbonyl, 2-pyridinylmethoxycarbonyl, 2-quinolinylcarbonyl;

B is valyl, isoleucyl or asparaginyl;

$R^1$ is 1,1-dimethylethyl or cyclopropyl; and

Y is phenyl, benzyl, phenoxy, 2-pyrimidinyloxy, 2,6-dimethyl-4-pyrimidinyloxy, benzyloxy, phenylthio, phenylsulfonyl, 2-pyridinylthio, 3-pyridinylthio, 4-pyridinylthio, 2-pyrimidinylthio, 4,6-dimethyl-2-pyrimidinylthio or ( 3-pyridinylmethyl ) thio; or a therapeutically acceptable acid addition salt thereof.

Another most preferred group of compounds is represented by formula 1 wherein X is (2-methylphenoxy)acetyl, (2,4-dimethylphenoxy)acetyl, (2,6-dimethylphenoxy)acetyl or 2,4,6-trimethylphenoxy)-acetyl;

B is absent;

$R^1$ is 1,1-dimethylethyl; and

Y is as defined in the last instance; or a therapeutically acceptable acid addition salt thereof.

Preferably, with reference to the compound of formula 1 in which B is the divalent radical —$NHCHR^4C(O)$—, the asymmetric carbon atom bearing $R^4$ has the (S) configuration.

Included within the scope of this invention is a pharmaceutical composition for treating HIV infections in a human comprising a compound of formula 1, or a therapeutically acceptable salt thereof, and a pharmaceutically acceptable carrier.

The scope of the invention includes as well a method for treating HIV infections in a human comprising administering thereto an effective amount of the compound of formula 1, or a therapeutically acceptable salt thereof.

Also included within the scope is a method for protecting human cells against HIV pathogenesis comprising treating said cells with an anti-HIV effective amount of a compound of formula 1, or a therapeutically acceptable salt thereof.

Processes for preparing the compounds formula 1 are described hereinafter.

DETAILS OF THE INVENTION

General

In general, the abbreviations used herein for designating the amino acids and the protective groups are based on recommendations of the IUPAC-IUB Commission of Biochemical Nomenclature, see European Journal of Biochemistry 138, 9 (1984). For instance, Val, Ile, Asn, and Leu represent the residues of L-valine, L-isoleucine, L-asparagine and L-leucine, respectively.

The term "lower alkyl" as used herein, either alone or in combination with a radical, means straight chain alkyl radicals containing one to six carbon atoms and branched chain alkyl radicals containing three to four carbon atoms and includes methyl, ethyl, propyl, butyl, hexyl, 1-methylethyl, 1-methylpropyl, 2-methylpropyl and 1,1-dimethylethyl.

The term "lower cycloalkyl" as used herein, either alone or in combination with a radical, means saturated cyclic hydrocarbon radical containing from three to six carbon atoms and includes cyclopropyl, cyclobutyl, cyclopentyl and cyclohexyl.

The term "lower alkoxy" as used herein means straight chain alkoxy radical containing one to six carbon atoms and branched chain alkoxy radicals containing three to four carbon atoms and includes methoxy, ethoxy, propoxy, hexoxy, 1-methylethoxy, butoxy and 1,1-dimethylethoxy. The latter radical is known commonly as tertiary-butyloxy.

The term "halo" as used herein means a halo radical selected from bromo, chloro, fluoro or iodo.

The term "Het" as used herein means a monovalent radical derived by removal of a hydrogen from a five- or six-membered saturated or unsaturated heterocycle containing from one to two heteroatoms selected from nitrogen, oxygen and sulfur. Optionally, the heterocycle may bear one or two substituents; for example, lower alkyl, lower alkoxy, halo, amino or lower alkylamino. Examples of suitable heterocylces and optionally substituted heterocycles include pyrrolidine, tetrahydrofuran, thiazolidine, pyrrole, 1H-imidazole, 1-methyl-1H-imidazole, isoxazole, thiazole, 2-methylthiazole, 2-aminothiazole, piperidine, 1,4-dioxane, 4-morpholine, pyridine, 2-methylpyridine, pyrimidine, 4-methylpyrimidine and 2,4-dimethylpyrimidine.

The term "residue" with reference to an amino acid means a radical derived from the corresponding α-amino acid by eliminating the hydroxyl of the carboxy group and one hydrogen of the α-amino group.

The term "pharmaceutically acceptable carrier" as used herein means a non-toxic, generally inert vehicle for the active ingredient, which does not adversely affect the ingredient.

The term "effective amount" as used herein means a predetermined amount of the compound of this invention sufficient to be effective against HIV in vivo.

In general, the compounds of formula 1 are prepared by known methods using reaction conditions which are known to be suitable for the reactants. Description of the methods are found in standard textbooks such as "Annual Reports In Organic Synthesis—1990", K. Turnbull et al., Eds, Academic Press, Inc., San Diego, Calif., U.S.A., 1990 (and the preceding annual reports), "Vogel's Textbook Of Practical Organic Chemistry", B. S. Furniss et al., Eds, Longman Group Limited, Essex, UK, 1986, and "The Peptides: Analysis, Synthesis, Biology", E. Grass et al., Eds, Academic Press, New York, N.Y., U.S.A., 1979–1987, Volumes 1 to 9.

More particularly, the compounds of formula 1 can be prepared by a process comprising: (a) reacting an epoxide of formula 2

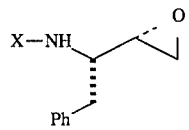

wherein X is as defined herein with pyrrolidinecarboxamide of formula 3

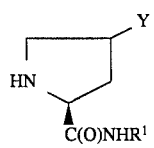

wherein $R^1$ and Y are as defined herein to obtain the corresponding compound of formula 1 wherein X, $R^1$ and Y are as defined herein and B is absent; or (b) reacting a compound of formula 4

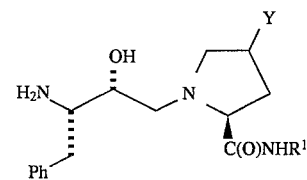

wherein $R^1$ and Y are as defined herein with a reactive derivative of the carboxylic acid X—OH wherein X is $R^2C(O)$ or $R^{24}OCH_2C(O)$ as defined herein to obtain the corresponding compound of formula 1 wherein X is $R^2C(O)$ or $R^{24}OCH_2C(O)$ as defined herein, $R^1$ and Y are as defined herein and B is absent; or (c) coupling the compound of formula 4 wherein $R^1$ and Y are as defined herein with an α-amino acid of the formula X—NHCHR$^4$COOH wherein X and $R^4$ are as defined herein in the presence of a coupling agent to obtain the corresponding compound of formula 1 wherein X, $R^1$ and Y are as defined herein and B is the divalent radical —NHCHR$^4$(O)— wherein $R^4$ is as defined herein; or (d) reacting a compound of formula 5

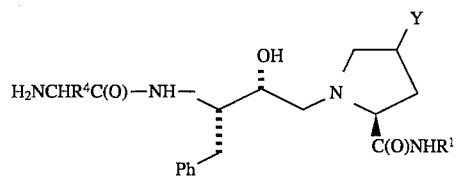

wherein $R^1$, $R^4$ and Y are as defined herein with a reactive derivative of the carboxylic acid X—OH wherein X is $R^2C(O)$ or $R^{24}OCH_2C(O)$ as defined herein to obtain the corresponding compound of formula 1 wherein X is $R^2C(O)$ or $R^{24}OCH_2C(O)$ as defined herein, $R^1$ and Y are as defined herein and B is the divalent radical —NHCHR$^4$C(O)— wherein $R^4$ is as defined herein; and (e) if desired, transforming the compound of formula 1, as obtained in the preceding sections (a), (b), (c) or (d), into a corresponding therapeutically acceptable acid addition salt.

It should be noted that the species of compounds of formula 1 in which X is a commonly used N-protective group, e.g. Boc, Z, Fmoc or p-methoxybenyloxycarbonyl, are obtained most readily and conveniently by processes (a) and (c). The ready accessibility of this species renders them useful as intermediates for a preferred route, via respective processes (b) and (d), to produce the respective compounds of formula 1 in which X is other than a commonly used N-protective group. As intermediates, therefore, the compounds of formula 1 of this species are deprotected (i.e. the protective group is removed), and the resulting N-terminal free amines are used as the respective compounds of formula 4 or formula 5 according to processes (b) and (d), depending on whether B is absent or present, for the ultimate preparation of the compounds of formula 1 in which X is other than a commonly used N-protective group, e.g. 2-pyridinylmethoxycarbonyl or 2-quinolinylcarbonyl.

More explicitly, according to the preceding process (a), the compounds of formula 1 in which B is absent can be prepared by an N-alkylation reaction involving the addition of the epoxide 2 to the pyrrolidinecarboxamide 3. The reaction can be effected conveniently by bringing the two reactants into contact in an inert solvent, e.g. ethanol, tetrahydrofuran or dimethylformamide, at temperatures ranging from 20° to 110° C. The reaction time is dependent on temperature and the nature of the reactants but generally ranges from two to 24 hours.

According to process (b), the compounds of formula 1 in which B is absent and X is $R^2C(O)$ or $R^{2A}OCH_2C(O)$ as defined herein are obtained by reacting the corresponding compound of formula 4 with a reactive derivative of the carboxylic acid X—OH wherein X is $R^2C(O)$ or $R^{2A}OCH_2C(O)$ as defined herein, respectively. Suitable reactive derivatives are the acylating agents capable of providing the appropriate acyl radical X—CO and include the corresponding acid halides, preferably the chlorides or bromides, active esters, anhydrides or mixed anhydrides. The reaction is performed according to known methods and conditions for accomplishing the reaction including the means to impart the desired selectivity to the reaction by choosing appropriate ratios of the reactants or by temporarily providing known protecting groups, if required, for any other reactive group competing with the intended reactive groups. Generally, the reaction is performed in an inert solvent, e.g. tetrahydrofuran, dimethylformamide or methylene dichloride, at a temperature between 0° and 50° C. and a reaction time ranging from 15 minutes to 24 hours.

According to process (c), the compounds of formula 1 in which B is the divalent radical —NHCHR$^4$C(O)— wherein R$^4$ is as defined herein can be obtained by coupling the compound of formula 4 with an α-amino acid of formula X—NHCHR$^4$COOH in the presence of a coupling agent. The use of coupling agents to promote the dehydrative coupling of a free carboxyl of one reactant with a free amino group of the other reactant is well known; for example, see "The Peptides: Analysis, Synthesis, Biology", Volumes 1 to 8, noted hereinbefore. Examples of suitable coupling agents are 1,1'-carbonyl-diimidazole or N,N'-dicyclohexyl-carbodiimide. Other examples are 1-hydroxybenzotriazole in the presence of N,N'-dicyclohexylcarbodiimide or N-ethyl-N'-[(3-dimethyl-amino)propyl]carbodiimide. A very practical and useful coupling agent is the commercially available (benzotriazol-1-yloxy)tris(dimethylamino)phosphonium hexafluorophosphate, either by itself or in the presence of 1-hydroxybenzotriazole. Still another very practical and useful coupling agent is the commercially available 2(1H-benzotriazol-1-yl)-N,N,N',N'-tetramethyluronium tetrafluoroborate.

The coupling reaction is conducted in an inert solvent, e.g. methylene dichloride, acetonitrile or dimethylformamide. An excess of an organic amine, e.g. diisopropylethylamine or N-methylmorpholine, is added to maintain the reaction mixture at a pH of about eight. The reaction temperature usually ranges from −20° to about 30° C. and reaction time from 15 minutes to eight hours.

With reference to process (d), this process is performed in the same manner as described hereinabove for process (b), the only exception being in the use of the compound of formula 5 instead of the compound of formula 4 as a starting material.

The epoxides of formula 2 used as starting materials for the process (a) are either known or can be prepared by known methods. More specifically the epoxides of formula 2 are either described by B. K. Handa et al., European patent application 346,847, published Dec. 20, 1989, or they can be made by methods described in the patent application.

The other starting materials for the processes, i.e. the pyrrolidinecarboxamides of formula 3, and the compounds of formulae 4 and 5, are novel and therefore are an object of this invention. Suitable processes for the preparation of the compounds of formulae 4 and 5 have been noted hereinbefore. The pyrrolidinecarboxamides of formula 3 can be prepared by standard amidation of known corresponding pyrrolidinecarboxylic acids. Alternatively, they can also be prepared by the method of F. Soucy, D. Wernic and P. Beaulieu, J. Chem. Soc. Perkins Trans. 1, 2885 (1991). Methods for producing the pyrrolidinecarboxamides of formula 3 are illustrated hereinafter in the examples.

The compound of formula 1 of this invention can be obtained in the form of a therapeutically acceptable acid addition salt. Examples of such salts are those with organic acids, e.g. acetic, lactic, succinic, benzoic, salicylic, methanesulfonic or p-toluenesulfonic acid, as well as polymeric acids such as tannic acid or carboxymethyl cellulose, and also salts with inorganic acids such as hydrohalic acids, e.g. hydrochloric acid, or sulfuric acid, or phosphoric acid. If desired, a particular acid addition salt is converted into another acid addition salt, such as a non-toxic, pharmaceutically acceptable salt, by treatment with the appropriate ion exchange resin in the manner described by R. A. Boissonnas et al., Helv. Chim. Acta, 43, 1849 (1960).

In general, the therapeutically acceptable salts of the peptides of formula 1 are biologically fully equivalent to the peptides themselves.

Biological Aspects

The HIV protease inhibiting properties and the cell protective effect against HIV pathogenesis of the compounds of formula 1, or a therapeutically acceptable salt thereof, can be demonstrated by biochemical, microbiological and biological procedures.

A particular useful procedure for demonstrating the HIV protease inhibiting properties of the compounds of formula 1 or their therapeutically acceptable salts is the "Recombinant HIV Protease HPLC Assay". The procedure is based on the capacity of the test compound to inhibit enzymatic cleavage by HIV protease of a decapeptide (the substrate) having an amino acid sequence which includes a known HIV protease cleavage site of a HIV polyprotein; see H. G. Krausslich et al., Proc. Natl. Acad. Sci. U.S.A., 86, 807 (1989). Details of this assay together with the results obtained for exemplified compounds of formula 1 are described in the examples hereinafter.

The capacity of the compounds of formula 1 or their therapeutically acceptable salts to protect cells against HIV infection can be demonstrated by microbiological procedures for evaluating the inhibitory effect of a test compound on the cytopathogenicity of HIV in human T4 cell lines. Typical of such procedures are those described by S. Harada and N. Yamamoto, Jpn. J. Cancer Res. (Gann), 76, 432 (1985), and S. Harada et al., Science, 229, 563 (1985). An assay based on the latter procedures is described in the examples hereinafter.

When a compound of this invention, or a therapeutically acceptable salt thereof, is used to combat HIV infections in a human, the peptide can be administered orally, topically or parenterally, in a vehicle comprising one or more pharmaceutically acceptable carriers, the proportion of which is determined by the solubility and chemical nature of the compound, the chosen route of administration and standard biological practice. For oral administration, the compound or a therapeutically acceptable salt thereof can be formulated in unit dosage forms such as capsules or tablets each containing a predetermined amount of the active ingredient, ranging from about 5 to 150 mg, in a pharmaceutically acceptable carrier. For topical administration, the compound can be formulated in a pharmaceutically acceptable vehicle containing 0.01 to 2 percent, preferably 0.05 to 1 percent, of the active agent. Such formulations can be in the form of a cream, lotion, sublingual tablet, or preferably a transdermal patch or buccal patch. For parenteral administration, the compound of formula 1 is administered by either intravenous, subcutaneous or intramuscular injection, in compositions with pharmaceutically acceptable vehicles or carriers. For administration by injection, it is preferred to use the compound in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations can be found in standard pharmaceutical texts, e.g. in "Remington's Pharmaceutical Sciences", 18th ed., Mack Publishing Company, Easton, Pa., 1990.

The dosage of the compound will vary with the form of administration and the particular active agent chosen. Furthermore, it will vary with the particular lost under treatment. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

For oral administration, the compound or a therapeutically acceptable salt is administered in the range of 5 to 150 mg per kilogram of body weight per day, with a preferred range of 5 to 50 mg per kilogram. With reference to systemic administration, the compound of formula 1 is administered at a dosage of 10 μg to 1000 μg per kilogram of body weight per day, although the aforementioned variations will occult.

Although the formulations disclosed hereinabove are effective and relatively safe medications for treating HIV infections, the possible concurrent administration of these formulations with other antiviral medications or agents to obtain beneficial results is not excluded. Such other antiviral medications or agents include soluble CD4, zidovudine, didanosine, zalcitabine, trisodium phosphonoformate, ribavarin, acyclovir, or antiviral interferons (e.g. α-interferon or interleukin-2).

The following examples illustrate further this invention solution percentages or ratios express a volume to volume relationship, unless stated otherwise. Temperatures are given in degrees Celsius. Proton nuclear magnetic resonance (NMR) spectra were recorded on a Bruker 200 MHz spectrometer; the chemical shifts (δ) are reported in parts per million. Abbreviations used in the examples include Boc: tert-butyloxycarbonyl; BOP: (benzotriazol-1-yloxy)tris-(dimethylamino)phosphonium hexafluorophosphate; Bu$^t$: tert-butyl; Bzl: benzyl; DIEA: diisopropylethylamine; DMF: dimethylformamide; HEPES: N-2-hydroxyethyl-piperazine-N'-2-ethanesulfonic acid; Et$_2$O: diethyl ether; EtOAc: ethyl acetate; EtOH: ethanol; HPLC: high performance liquid chromatography; MeOH: methanol; Ph: phenyl; THF: tetrahydrofuran; Z: benzyloxycarbonyl.

EXAMPLE 1

Preparation of 4(S)-Benzyloxy-N-tert-butyl-1-(tert-butyloxycarbonyl) pyrrolidine-2(S)-carboxamide (a) The N-protected acid, 1-(tert-butyloxycarbonyl)-4(S)-hydroxypyrrolidine-2(S)-carboxylic acid, was prepared by reacting 4(S)-hydroxypyrrolidine-(S)-carboxylic acid {cis-4-hydroxy-L-proline, described by S. G. Ramaswamy and E. Adams, J. Org. Chem., 42, 3440 (1977)} with di-tert-butyl carbonate in the presence of excess NaOH in a THF/H$_2$O (1:1) solution at room temperature for 18 h.

(b) The N-protected acid (400 mg, 1.73 mmol) so obtained was dissolved in DMF (7 mL). Sodium hydride (99%, 87 mg, 3.63 mmol) was added to the solution. The mixture was stirred at room temperature (20°–22°) for 2 h. Benzyl bromide (1.03 mL, 8.65 mmol) was added and the mixture was stirred at room temperature for 18 h. Thereafter, the mixture was diluted with EtOAc, cooled to 0° C. and rendered acidic (pH3) by the addition of 10% aqueous citric acid. The organic layer was separated, washed with H$_2$O and brine, dried (MgSO$_4$), and concentrated to dryness under reduced pressure. The residual yellow oil was purified by chromatography (SiO$_2$, eluent: hexane-EtOAc, 9:1) to give 4(S)-benzyloxy-1-(tert-butyloxycarbonyl)pyrrolidine-2(S)-carboxylic acid benzyl ester (301 mg, 70%).

(c) The latter compound (301 mg, 0.73 mmol) was dissolved in MeOH/H$_2$O (2:1, 4 mL). The solution was stirred and cooled to 0° C. An aqueous 2M solution of NaOH (1.16 mL) was added. After 10 min, the mixture was allowed to warm to room temperature and then stirred for 18 h at the same temperature. Thereafter, the reaction was diluted with Et$_2$O/hexane (1:1, 10 mL) and H$_2$O (5 mL). The aqueous layer was separated, extracted twice with Et$_2$O/hexane (1:1), cooled to 0° C., rendered acidic (pH 3) with 10% aqueous citric acid and extracted with EtOAc (3×). The combined EtOAc extracts were washed with H$_2$O (2×) and brine, dried (MgSO$_4$) and concentrated under reduced pressure. The residue was dried under high vacuum to give a quantitative yield of 4(S)-benzyloxy-1-(tert-butyloxycarbonyl)-pyrrolidine-2(S)-carboxylic acid.

(d) To a 0.2M solution of the latter compound (234.7 mg, 0.73 mmol) in CH$_2$Cl$_2$ was added DIEA (127 μL, 0.73 μmol), followed by the addition of tertbutylamine (84.4 μL, 0.803 mmol) and BOP (387 mg, 0.876 mmol). The reaction mixture was stirred at room temperature for 3 h while its pH was maintained at 8 by periodic verification and by the addition of DIEA as required. Thereafter, the reaction mixture was diluted with EtOAc and washed successively with a saturated aqueous solution of NaHCO$_3$ (2×), H$_2$O and brine. The organic layer was dried (MgSO$_4$) and concentrated to dryness under reduced pressure. The resulting yellow oil was purified by flash chromatography (SiO$_2$, eluent: hexane-EtOAc, 7:3 then 6:4) to give the title compound (252 mg, 92%). $^1$NMR (CDCl$_3$) δ 7.40–7.25 (m, 5H), 6.05 (broad s, 1H), 4.6–4.35 (broad d, 2H), 4.2–4.05 (m, 2H), 3.8–3.55 (m, 2H) 2.55–2.1 (m, 2H) 1.46 (s, 9H), 1.20 (broad s, 9H).

EXAMPLE 2

Preparation of 1-{3(S)-Amino-2(R)-hydroxy-4-phenylbutyl}-4(S)-benzyloxy-N-tert-butylpyrrolidine-2(S)-carboxamide (formula 4: R$^1$=C(CH$_3$)$_3$ and Y=OCH$_2$Ph; C(O)NHR$^1$/Y=cis)

(a) A solution of the title compound of example 1 (250 mg, 0.664 mmol) in 6N HCl/dioxane was stirred at room temperature for 20 min and then concentrated to dryness under reduced pressure. The residue was diluted with EtOAc (10 mL) and 2 N aqueous NaOH (3 mL). The mixture was stirred at room temperature for 15 min. The organic layer was separated, washed with a minimum amount of H$_2$O and brine, dried (MgSO$_4$) under reduced pressure. The residue was dried under high vacuum to give 4(S)-benzyloxy-N-tert-butylpyrrolidine-2(S)-carboxamide, the carboxamide of formula 3 wherein $R^1$ is $C(CH_3)_3$ and Y is $OCH_2Ph$ {$C(O)NHR^1/Y$=cis}.

(b) The latter compound was mixed in absolute EtOH (5 mL) with 3(S)-(benzyloxycarbonyl)-1,2(S)-epoxy-4-phenylbutane (180 mg, 0.604 mmol), namely the epoxide of formula 2 in which X is Z, see B. K. Handa et al., supra. The mixture was heated at reflux for 18 h and then concentrated to dryness under reduced pressure. The residue was purified by flash chromatography ($SiO_2$, eluent: $CHCl_3$—MeOH, 39:1 then 19:1) to give 4(S)-benzyloxy-1-{3(S)-{(benzyloxycarbonyl)amino}-2(R)-hydroxy-4-phenylbutyl}-N-tert-butylpyrrolidine-2(S)-carboxamide (220 mg, 63%) as a white foam.

(c) The latter compound (220 mg, 0.384 mmol) was subjected to hydrogenolysis (5% Pd/C, 1 atmosphere of $H_2$, MeOH, 3.5 h) to give the title compound which was used immediately according to the coupling procedure of the following example.

EXAMPLE 3

Preparation of
4(S)-Benzyloxy-1-{3(S)-{{N-(benzyloxycarbonyl)
valyl}amino}-2(R)-hydroxy-4-phenylbutyl}-
N-tert-butylpyrrolidine-2(S)-carboxamide (formula
1: X=Z, B=Val, $R^1=C(CH_3)_3$ and Y=$OCH_2Ph$;
$C(O)NHR^1/Y$=cis)

The title compound was prepared according to the following coupling procedure:

DIEA (33.4 μL, 0.192 mmol), the protected amino acid Z—Val—OH (53.1 mg, 0.211 mmol) and BOP (102 mg, 0.23 mmol) were added to a 0.2M solution of the title compound of example 2 (0.192 mmol) in $CH_2Cl_2$. The reaction mixture was maintained at pH 8 by periodic verification and by the addition of DIEA as required, while the mixture was stirred at room temperature for 2 h. Thereafter, the reaction mixture was diluted with EtOAc, washed successively with a saturated aqueous solution of $NaHCO_3$ (2×), $H_2O$ and brine. The organic layer was dried ($MgSO_4$) and concentrated under reduced pressure. The residue was purified by flash chromatography ($SiO_2$, eluent: $CHCl_3$—MeOH, 39:1) to give the title compound of this example as a white solid (108 mg, 83%). FAB mass spectrum, m/z: 673.3 $(M+H)^+$.

EXAMPLE 4

Preparation of
4(R)-Benzyloxy-1-{3(S)-{{N-(benzyloxycarbonyl)
valyl}amino}-2(R)-hydroxy-4phenylbutyl}-
N-tert-butylpyrrolidine-2(S)-carboxamide (formula
1: X=Z, B=Val, $R^1=C(CH_3)_3$ and Y=$OCH_2Ph$;
$C(O)NHR^1/Y$=trans)

By following serially the procedures of examples 1,2 and 3, but in the procedure of section (a) of example 1 replacing 4(S)-hydroxypyrrolidine-2(S)-carboxylic acid with an equivalent amount of 4(R)-hydroxypyrrolidine-2(S)-carboxylic acid (trans-4-hydroxyproline-2-carboxylic acid), see S. G. Ramaswamy and E. Adams, supra), the title compound was obtained. FAB mass spectrum, m/z: 673.3 $(M+H)^+$.

EXAMPLE 5

Preparation of
4(R)-Benzyloxy1-{3(S)-{{N-(benzyloxycarbonyl)
asparaginyl}amino}-2(R)-hydroxy-4-
phenylbutyl}-N-tert-butylpyrrolidine-
2(S)-carboxamide (formula 1: X=Z, B=Asn,
$R^1=C(CH_3)_3$ and Y=$OCH_2Ph$; $C(O)NHR^1/Y$=trans)

By following serially the procedures of examples 1 and 2, but in the procedure of section (a) of example 1 replacing 4(S)-hydroxypyrrolidine-2(S)-carboxylic acid with an equivalent amount of 4(R)-hydroxypyrrolidine-2(S)-carboxylic acid, and subjecting 1-{3(S)-amino-2(R)-hydroxy-4-phenylbutyl}-4(R)-benzyloxy-N-tert-butylpyrrolidine-2(S)carboxamide, thus obtained, to the following coupling procedure, the title compound was obtained.

1-Hydroxybenzotriazole (20.1 mg, 0.148 mmol) was added to a cooled (0°) solution of N,N'-dicyclohexylcarbodiimide (34 mg, 0.165 mmol) in THF (2 mL). The mixture was stirred for 15 min. A solution of the protected amino acid Z—Asn—OH (395 mg, 0.148 mmol) in DMF (1 mL) and a solution of the previously noted 1-{3(S)-amino-2(R)-hydroxy-4-phenylbutyl}-4(R)-benzyloxy-N-tert-butylpyrrolidine-2(S)-carboxamide (35.4 mg, 0.083 mmol) in DMF (1 mL) was added to the mixture. The mixture was allowed to warm slowly to room temperature and then stirred for 18 h. Thereafter, the mixture was diluted with EtOAc. The organic phase was separated, washed with a saturated aqueous solution of $NaHCO_3$, $H_2O$ and brine, dried ($MgSO_4$), and concentrated to dryness under reduced pressure. The white solid residue was purified by flash chromatography ($SiO_2$, eluent: EtOAc/MeOH, 97:3 then 19:1) to give the title compound of this example. EI mass spectrum, m/e: 689.2 $(M+2H)^+$.

(Note that the preceding exemplified coupling procedure using 1-hydroxybenzotriazole in the presence of N,N'-dicyclohexylcarbodiimide represents a preferred coupling procedure for the preparation of compounds of formula 1 in which B is the amino acid residue Asn.)

EXAMPLE 6

Preparation of 4(S)-Benzyloxy-1-{3(S)-{{N-
benzyloxycarbonyl)asparaginyl}amino}-
2(R)-hydroxy-4-phenylbutyl}-
N-tert-butylpyrrolidine-2(S)-carboxamide (formula
1: X=Z, B=Asn, $R^1=C(CH_3)_3$ and Y=$OCH_2Ph$;
$C(O)NHR^1/Y$=cis)

By following serially the procedures of example 1 and 2, and the coupling procedure of example 5, the title compound was obtained. FAB mass spectrum, m/z: 688.4 $(M+H)^+$; 710.4 $(M+Na)^+$.

EXAMPLE 7

Preparation of
1-{3(S)-{{N-(benzyloxycarbonyl)valyl}amino}-
2(R)-hydroxy-4-phenylbutyl}-N-tert-butyl-
4(S)-(2-methylpropyloxy)pyrrolidine
-2(S)-carboxamide {formula 1: X=Z, B=Val, $R^1=C(CH_3)_3$ and Y=$OCH_2CH(CH_3)_2$; $C(O)NHR^1/Y$=cis}

By following serially the procedures of examples 1, 2 and 3, but replacing benzyl bromide with an equivalent amount of 2-methylpropyl bromide in the procedure of section (b) of example 1, the title compound was obtained. EI mass spectrum, m/e: 583.4 (MH$_2$-C$_4$H$_9$)$^+$.

EXAMPLE 8

Preparation of
1-{3(S)-{{N-(benzyloxycarbonyl)valyl}amino}-
2(R)-hydroxy-4-phenylbutyl}-N-tert-butyl-
4(R)-(2-methylpropoxy)pyrrolidine-
2(S)-carboxamide {formula 1: X=Z, B=Val,
R$^1$=C(CH$_3$)$_3$ and Y=OCH$_2$CH(CH$_3$)$_2$;
C(O)NHR$^1$/Y=trans}

By following serially the procedures of example 1, 2 and 3, but in the procedure of section (a) of example 1 replacing 4(S)-hydroxypyrrolidine-2(S)-carboxylic acid with an equivalent amount of 4(R)-hydroxypyrrolidine-2(S)-carboxylic, and in the procedure of section (b) of example 1 replacing benzyl bromide with an equivalent amount of 2-methylpropyl bromide, the title compound was obtained. EI mass spectrum, m/e: 583.3 (MH$_2$-C$_4$H$_9$)$^+$.

EXAMPLE 9

Preparation of
4(R)-Benzyloxy-1-{3(S)-{{N-(benzyloxycarbonyl)
valyl}amino}-2(R)-hydroxy-4-phenylbutyl}-
N-cyclopropylpyrrolidine-2(S)-carboxamide
(formula 1: X=Z, B Val,=R$^1$=cyclopropyl and
Y=OCH$_2$Ph; C(O)NHR$^1$/Y=trans)

By following serially the procedures of examples 1, 2 and 3, but in section (a) of example 1 replacing 4(S)-hydroxypyrrolidine-2(S)-carboxylic acid with an equivalent amount of 4(R)-hydroxypyrrolidine-2(S)-carboxylic acid and in section (d) of example 1 replacing tert-butylamine with an equivalent amount of cyclopropylamine, the title compound was obtained. EI mass spectrum, m/e: 657.5 (M+H)$^+$.

EXAMPLE 10

Preparation of the 4(R,S), 4(R) and 4(S) Isomers of
4-Benzyl-1-{3
(S)-{{N-(benzyloxycarbonyl)-asparaginyl}amino}-
2(R)-hydroxy-4-phenylbutyl}-N-tert-
butylpyrrolidine-2(S)-carboxamide (formula 1:
X=Z, B=Asn, R$^1$=C(CH$_3$)$_3$ and Y=Bzl)

By applying the method described by F. Soucy, D. Wernic and P. Beaulieu, supra, a mixture of the 4(R) and 4(S) diastereoisomers of 4-benzyl-1-(tert-butyloxycarbonyl)pyrrolidine-2(S)-carboxylic acid (3:2, w/w) was obtained from serine lactone and 3-phenyl-2-propenyl bromide. Coupling of the diastereoisomeric mixture with tert-butylamine in the presence of BOP according to the procedure of section (d) of example 1 gave a corresponding diastereoisomeric mixture of the 4(R) and 4(S) isomers of 4-benzyl-N-tert-butyl-1-(tert-butyloxy-carbonyl)pyrrolidine-2(S)-carboxamide. Thereafter, by following the procedures of sections (b) of example 2 and using the latter diastereoisomeric mixture as the carboxamide of formula 3, a corresponding diastereoisomeric mixture of the 4(R) and 4(S) isomers of 4-benzyl-1-{3(S)- {(benzyloxycarbonyl)-amino}-2(R)-hydroxy-4-phenylbutyl}- N-tert-butylpyrrolidine-2(S)-carboxamide was obtained. FAB mass spectrum, m/z: 558 (M+H)$^+$. In turn, reaction of the latter diastereoisomeric mixture with the N-protected amino acid Z—Asn—OH according to the coupling procedure of example 5, gave a corresponding diastereoisomeric mixture of the 4R and 4S isomers of 4-benzyl-1-{3(S)- {{N-(benzyloxycarbonyl)asparaginyl}amino}-2(R)-hydroxy-4-phenylbutyl}-N-tert-butylpyrrolidine-2(S)-carboxamide. FAB Mass spectrum, m/z: 672 (M+H)$^+$.

The two isomers were separated by HPLC techniques to give the corresponding pure 4R and 4S isomers. More specifically exemplified, a 20 mg sample of the last mentioned mixture dissolved in 2.5 mL of 50% aqueous acetic acid (initial conditions), was loaded onto a Whatman Magnum 9®, C$_{18}$ octadecyl silyl column (0.94×50 cm). Initial column equilibration conditions were as follows: 10% A and 90% B (Pump A: 0.06% trifluoroacetic acid in acetonitrile; Pump B: 0.06% trifluoroacetic acid in H$_2$O). Once the peak corresponding to acetic acid (at the solvent front) had passed, a linear gradient ensued. The isomer separation program was as follows: 10–30% A for 5 min, 30% A for 10 min, then 30–100% A for 110 min, at 3 mL/min and 230 nm. The 4(R) isomer and the 4(S) isomer were collected at 60% A (9.2 mg) and 63% A (8.3 mg), respectively.

EXAMPLE 11

Preparation of
N-tert-Butyl-1-{2(R)-hydroxy-4-phenyl-3(S)-{{N-2-
quinolinylcarbonyl)valyl}amino}butyl}-4(R)-
(2-pyrimidinylthio)pyrrolidine-2(S)- carboxamide
(formula 1; X=2-quinolinylcarbonyl, B=Val, R$^1$=C
(CH$_3$)$_3$ and Y=2-pyrimidinylthio)

(a) The N-protected acid (17.5 g, 75.6 mmol, described in section (a) of example 1) was dissolved in CH$_2$Cl$_2$ (300 mL) and DIEA (13 mL, 76.6 mmol). tert-Butylamine (8.73 mL, 83.1 mmol ) was added to the solution, followed by the addition of BOP (40 g, 90.7 mmol) and DIEA (13 mL, 151 mmol). The mixture was stirred at room temperature for 7 h and then diluted with EtOAc. The organic phase was separated, washed with a saturated aqueous solution of NaHCO$_3$ (2×), H$_2$O (2×) and brine (2×), dried (MgSO$_4$) and evaporated to dryness. The solid residue was triturated with Et$_2$O/EtOAc (9:1), collected on a filter, washed with Et$_2$O and dried to provide N-tert-butyl-1-(tert-butyloxycarbonyl)-4(R)-hydroxypyrrolidine-2(S)-carboxamide (15.6 g, 72%).

(b) The latter compound (5.0 g, 17.5 mmol) was dissolved in toluene/THF (3:1, 175 mL). Triphenylphosphine (5.72 g, 21.8 mmol) and imidazole (1.08 g, 30.5 mmol) were added to the solution at room temperature. The mixture was warmed to 45°–50°. Iodine (5.54 g, 21.8 mmol) was added and the mixture was stirred vigorously for 80 min at 45°–50°. Thereafter, the reaction mixture was cooled and diluted with Et$_2$O and H$_2$O. The organic layer was separated, washed with a saturated aqueous solution of NaHCO$_3$ (1×) and brine (1×), dried (MgSO$_4$) and evaporated to dryness to give a brown oil containing some solid (triphenylphosphine oxide). The oily solid was triturated with Et$_2$O and the solid collected on a filter. The filtrate was evaporated to dryness to give a brown oil. The oil was purified by flash chromatography (SiO$_2$, eluent: EtOAc/hexane, 1:4) to give N-tert-butyl-1-(tert-butyloxycarbonyl)-4(S)-iodopyrrolidine-2(S)-carboxamide as a yellow solid (4.83 g, 70%). $^1$NMR (CDCl$_3$) δ 6.2–6.0 (broad s, 1H), 4.27–4.0 (m, 3H), 3.75–3.55 (m, 1H), 2.9–2.5 (m, 2H), 1.47 (s, 9H), 1.38 (s, 9H).

(c) 2-Pyrimidinethiol (1.06 g, 9.46 mmol) was added portionwise to a cooled (0°) suspension of sodium hydride (99%, 182 mg, 7.57 mmol) in DMF (10 mL). The mixture was stirred at the same temperature for 30 min. Thereafter, a solution of the product the preceding section (b) (1.5 g, 3.79 mmol) in DMF (5 mL) was added dropwise to the mixture. The reaction mixture was stirred at room temperature for 18 h and then diluted with EtOAc and H$_2$O. The organic phase was separated, washed with cold H$_2$O (1×), a 1N aqueous solution of NaOH (2×) and brine (1×), dried (MgSO$_4$) and evaporated to dryness to give a solid. Trituration of the solid with Et$_2$O gave N-tert-butyl-1-(tert-butyloxycarbonyl)-4(R)-(2-pyrimidinylthio)pyrrolidine-2(S)-carboxamide as off-white solid. $^1$H NMR (CDCl$_3$) δ 8.53–8.51 (d, J=4.85 Hz, 2H), 7.01–6.96 (t, J=4.85, 10.0 Hz, 1H), 5.97–5.75 (broad s, 1H), 4.4–4.2 (m, 2H), 4.1–3.91 (m, 1H), 3.70–3.35 (m, 2H), 2.92–2.75 (m, 1H), 1.47 (s, 9H), 1.36 (s, 9H). FAB mass spectrum (m/z): 381 (M+H)$^+$, 403 (M+Na)$^+$.

(d) The latter compound was deprotected and reacted with the epoxide of formula 2 in which X is Boc according to the procedure of sections (a) and (b) of example 2 to give N-tert-butyl-1-{3(S)-{(tert-butyloxycarbonyl)amino}-2(R)-hydroxy-4-phenylbutyl}-4(R)-(2-pyrimidinylthio)pyrrolidine-2(S)-carboxamide FAB mass spectrum, m/z: 544 (M+H)$^+$, 566 (M+Na)$^+$. In turn, the latter compound was deprotected according to procedure of section (a) of example 2 and coupled with Boc—Val—OH according to the procedure of example 3 to give N-tert-butyl-1-{3(S)-{{N-(tert-butyloxycarbonyl)valyl}amino}-2(R)-hydroxy-4-phenylbutyl}-4(R)- (2-pyrimidinylthio)pyrrolidine-2(S)-carboxamide. FAB mass spectrum (m/z): 643 (M+H)$^+$, 665 (M+Na)$^+$.

(e) A solution of the latter compound (887 mg, 1.38 20 mmol) in 6N HCl/dioxane (7 mL) was stirred at room temperature for 20 min. The solvent was removed under reduced pressure. The residue, a white solid, was dried under high vacuum for 20 min to give the corresponding deprotected amine as a hydrochloride salt. The latter salt was dissolved in CH$_2$Cl$_2$ (7 mL and DIEA (481 µL, 2.76 mmol). 2-Quinolinecarboxylic acid (263 mg, 1.52 mmol) and BOP (732 mg, 1.66 mmol) were added to the solution of the salt. The reaction mixture was stirred at room temperature for 5 h while the pH of the mixture was maintained at 8 by periodic verification and the addition of DIEA when required. Thereafter, the reaction mixture was diluted with EtOAc and washed successively with a saturated aqueous solution of NaHCO$_3$ (2×), H$_2$O and brine. The organic layer was dried (MgSO$_4$) and concentrated to dryness under reduced pressure. The resulting colorless oil was purified by flash chromatography (SiO$_2$, eluent: hexane-EtOAc, 3:7 and then 1:9) to give the title compound as a white foam (750 mg, 78%). Trituration of the foam with Et$_2$O gave the title compound as a white solid (378 mg, 40%) FAB mass spectrum, m/z: 698 (M+H)$^+$, 720 (M+Na)$^+$. The NMR of the compound conformed with the assigned structure.

By following the procedure of this example but replacing 2-pyrimidinethiol in section (c) with 3-pyridinemethanethiol, N-tert-butyl-1-{2(R)-hydroxy-4-phenyl-3(S)- {{N-(2-quinolinylcarbonyl)valyl}amino}butyl}-4(R)- {(3-pyridinylmethyl)thio}pyrrolidine-2(S)-carboxamide is obtained. FAB mass spectrum, m/z: 711 (M+H)$^+$, 733 (M+Na)$^+$.

Again, by following the procedure of this example but replacing 2-pyrimidinethiol in section (c) with 2,6-dimethyl-4-hydroxypyrimidine, N-tert-butyl-1-{2(R)-hydroxy-4-phenyl-3(S)-{{N-(2-quinolyinylcarbonyl)valyl}amino}butyl}-4(R)-{(2,6-dimethyl-4-pyrimidinyl)oxy}pyrrolidine-2(S)-carboxamide is obtained. FAB mass spectrum/z: 710 (M+H), 586 (M+H–C$_6$H$_8$N$_2$O)$^+$.

EXAMPLE 12

Preparation of
N-tert-Butyl-1-{3(S)-{{(2,6-dimethylphenoxy)acetyl} amino}-2(R)-hydroxy-4-phenylbutyl}-4(R)- (2-pyrimidinylthio)pyrrolidine-2(S)-carboxamide (formula 1; X=(2,6-dimethylphenoxy)acetyl, B is absent, R$^1$=C(CH$_3$)$_3$ and Y is 2-pyrimidinylthio)

N-tert-Butyl-1-{3(S)-{N-(tert-butyloxycarbonyl)amino}-2(R)-hydroxy-4-phenylbutyl}-4(R)-(2-pyrimidinylthio)pyrrolidine-2(S)-carboxamide, described in section (d) of example 11, was converted to its corresponding primary amine, i.e. N-tert-butyl-1-(3(S)-amino-2(R)-hydroxy-4-phenylbutyl)-4(R)-(2-pyrimidinylthio)pyrrolidine -2-carboxamide, by removal of the Boc protecting group in the usual manner. The latter compound was coupled with (2,6-dimethylphenoxy)acetic acid according to the procedure of example 3 to give the title compound. FAB mass spectrum, m/z: 606 (M+H)$^+$, 628 (M+Na)$^+$.

By following the procedure of this example but replacing the primary amine with the corresponding primary amine, N-tert-butyl-1-(3(S)-amino-2(R)-hydroxy-4-phenylbutyl)-4(R)-{(3-pyridinylmethyl)thio}pyrrolidine-2-carboxamide (used as an intermediate for N-tert-butyl-1-{2(R)-hydroxy-4-phenyl-3(S)- {{N-(2-quinolinylcarbonyl)valyl} amino}butyl}-4(R)-{(3-pyridinylmethyl)thio}pyrrolidine-2(S)-carboxamide of example 11), N-tert-butyl-1{3(S)-{{2,6-dimethylphenoxy)acetyl}amino}-2(R)-hydroxy-4-phenylbutyl}-4(R)-{(3-pyridinylmethyl)thio}pyrrolidine-2(S)-carboxamide, FAB mass spectrum, m/z: 619 (M+H)$^+$, 641 (M+Na)$^+$, is obtained.

EXAMPLE 13

Recombinant HIV Protease HPLC Assay

Enzyme: HIV protease was expressed in *E. coli* {construct pBRT1 prt$^+$, see W. G. Farmerie et al., Science, 236, 305 (1987)}, according to the following protocol: Unless stated otherwise, all solutions are aqueous solutions.
(i) Fermentation

*E. coli* cells containing the pBRT1 prt$^+$plasmid were used to inoculate a seed culture media composed of Luria-Bertani Broth containing 100 µg/mL of ampicillin. Flasks were incubated at 37° under agitation for 17 h. Production flasks containing sterile M9 broth, supplemented with 100 µg/mL of ampicillin, were inoculated at a level of 1% (v/v) using the seed culture described above. Total volume in each production flask was 500 mL in a 2 L Erlenmeyer flask. Flasks were incubated at 37° under agitation until a cell concentration corresponding to an optical density (λ=540 µm) of 0.6 was reached (no dilution). This time span was routinely 3–4 h. Flasks were then supplemented with 5 mM isopropylthiogalactoside (IPTG, Research Organics, Cleveland, Ohio, USA) and incubation was continued until the cell concentration reached an optical density of 0.2 at 16-fold dilution. Flasks were then supplemented with 1 mM phenylmethylsulfonyl fluoride (PMSF) and rapidly chilled to 4°. The bacterial cells were recovered by centrifugation at 4°. The wet pellet was stored at −70°.
(ii) Extraction and Preparation of Assay Grade Enzyme All steps below were perfomed at 4° unless otherwise indicated. Thawed cells were mixed with buffer A {50 mM tris(hydroxymethyl)aminoethane HCl (Tris-HCl, pH 7.4); 0.6 mM ethylenediaminetetraacetic acid (EDTA); 0.375M NaCl, 0.2% Nonidet P-40® (BDH Chemicals Ltd., Poole, UK); 1 mM PMSF}, at a ratio of one part cells to nine parts buffer A. Diatomaceous earth (Celite 545® John Manville, Lompoc, Calif. U.S.A.) was added at a ratio of two parts to one part of wet cell weight. The resulting slurry was homogenized at high speed (ca. 20,000 rpm) on a Waring® industrial blender for 8×15 sec. pulses. Cell debris/Celite® was collected by centrifugation and the resulting pellet was extracted with 4.5 parts of buffer A to one part wet solids using the homogenization procedure described above. Supernatants from both homogenization steps were combined and soluble protein was precipitated by the addition of solid $(NH_4)_2SO_4$ to yield a final concentration of 75% saturation. This mixture was agitated for 60 min and the precipitate was recovered by centrifugation. The resulting pellet was suspended in buffer B {50 mM Tris-HCl, pH 8; 30 mM NaCl; 1 mM DL-dithiothreitol (DTT); 1 mM EDTA; mM PMSF; 10% glycerol}, and dialyzed for 18 h against the same buffer.

An aliquot of the dialyzed extract containing 150 mg of the protein was loaded onto a Sephadex A25® anion exchange column (Pharmacia, Uppsala, Sweden) with bed dimensions of 70 cm length and 2.5 cm diameter. The sample was eluted isocratically with buffer B at a linear flow rate of 10 cm/h. Fractions containing HIV protease activity (see below for assay description) were combined, and soluble protein was precipitated by the addition of saturated aqueous $(NH_4)_2SO_4$ to yield a total $(NH_4)_2SO_4$ concentration of 85% saturation. Precipitated protein was removed by centrifugation and the resulting pellet was dissolved in buffer C {50 mM 2-(4-morpholino)ethanesulfonic acid (MES), pH 5.5; 150 mM NaCl; 1 mM DTT; 1 mM EDTA; 10% glycerol}. This preparation was dialyzed for 18 h against buffer C, and then frozen at −70°. All crude extracts were purified by chromatography in aliquots containing 150 mg of protein in the same manner as described above. The final preparations from each batch were pooled, divided into 34 µL aliquots and stored at −70°. The final protein recovered from a 20 L fermentation was typically 300 mg with a specific activity for HIV protease of 18.2 mmoles of substrate cleaved/min/mg.

The aliquots were diluted to 1/38 of the original concentration with buffer, see below, prior to use (i.e. the enzyme working solution).

Substrate: VSFNFPQITL—$NH_2$, MW 1164, see Krausslich et al., Proc. Natl. Acad. Sci. USA, 86, 807 (1989), was used as substrate. The substrate was made into 10 mM stock in DMSO and stored at 4°. Prior to use, the stock was diluted with buffer to give a 400 µM solution (i.e. the substrate working solution).

Buffer: MES (100 mM), KCl (300 mM) and EDTA (5 mM) were dissolved in distilled $H_2O$ (90 mL) and the solution was adjusted to pH 5.5 with concentrated aqueous NaOH. The latter solution was diluted to 100 mL with $H_2O$ to give the buffer.

Procedure: (1) The assay mixture was prepared by mixing 20 µL of the substrate working solution, 10 µL of the solution of the test compound in 10% DMSO and 10 µL of the enzyme working solution. (2) The assay mixture was incubated at 37° for 30 min. (3) The reaction was quenched by adding 200 µL of 2% aqueous trifluoroacetic acid. (4) The substrate and products (i.e. VSFNF and PQITL—$NH_2$) were separated by subjecting 100 ML of the quenched assay mixture to HPLC using a Perkin-Elmer 3×3 CRC8 column (Perkin Elmer Inc., Norwalk, Conn., USA) with a stepwise gradient at a flow rate of 4 mL/min. The gradient is as follows:

0.0–0.5 minutes, 70% A/30% B;
0.5–3.0 minutes, 67% A/33% B;
3.0–5.0 minutes, 20% A/80% B;
5.0–6.5 minutes, 70% A/30% B;

where A is 3 mM sodium dodecyl sulfate/0.05% $H_3PO_4$ in $H_2O$ and B is 0.05% $H_3PO_4$ in acetonitrile. Elution was monitored at 210 nM. (5) A control, which was the assay mixture without the test compound, was subjected simultaneously to steps 2 to 4.

Inhibition Studies: Cleavage products and remaining parent substrate were quantified by either peak height or by integration of the appropriate HPLC peaks. Substrate conversion was calculated using the following relationship:

$$\% \text{ Conversion} = \frac{\text{Sum of peak height or peak area of products}}{\text{Sum of peak height or peak area of substrate and products}} \times 100$$

Enzyme inhibition of the test compound was calculated as follows:

$$\% \text{ Inhibition} = 100 - \frac{\% \text{ Conversion for assay mixture}}{\% \text{ Conversion of control}} \times 100$$

The concentration of the test compound which causes a 50% inhibition of the HIV-protease, i.e. the $IC_{50}$, was determined as follows: The percent inhibition of the enzyme was determined for a minimum of three different concentrations of the test compound. Thereafter, the $IC_{50}$ was determined graphically by plotting the percent inhibition of the enzyme against the concentration of the test compound.

The $IC_{50}$'s of exemplified compounds of formula 1, as determined in the recombinant HIV protease HPLC assay, are listed in the following Table.

TABLE I

| ENTRY NO. | COMPOUND | $IC_{50}$ (nM) |
|---|---|---|
| 1 | 4(S)-Benzyloxy-1-{3(S)-{{N-(benzyloxycarbonyl)valyl}-amino}-2(R)-hydroxy-4-phenylbutyl}-N-tert-butyl-pyrrolidine-2(S)-carboxamide | 150 |
| 2 | 4(R)-Benzyloxy-1-{3(S)-{{N-(benzyloxycarbonyl)valyl}-amino}-2(R)-hydroxy-4-phenyl-butyl}-N-tert-butylpyrrolidine-2(S)-carboxamide | 16 |
| 3 | 4(R)-Benzyloxy-1-{3(S)-{{N-(benzyloxycarbonyl)asparaginyl}amino}-2(R)-hydroxy-4-phenylbutyl}-N-tert-butyl-pyrrolidine-2(S)-carboxamide | 39 |
| 4 | 4(S)-Benzyloxy-1-{3(S)-{{N-(benzyloxycarbonyl)asparaginyl}amino}-2(R)-hydroxy-4-phenylbutyl}-N-tert-butyl-pyrrolidine-2(S)-carboxamide | 300 |
| 5 | 1-{3(S)-{{N-(benzyloxycarbonyl)valyl}amino}-2(R)-hydroxy-4-phenylbutyl}-N-tert-butyl-4(S)-(2-methylpropyloxy)pyrrolidine-2(S)-carboxamide | 745 |
| 6 | 1-{3(S)-{{N-(benzyloxycarbonyl)valyl}amino}-2(R)-hydroxy-4-phenylbutyl}-N-tert-butyl-4(R)-(2-methylpropyloxy)pyrrolidine-2(S)-carboxamide | 180 |
| 7 | 4(R)-Benzyloxy-1-{3(S)-{{N-(benzyloxycarbonyl)valyl}amino}-2(R)-hydroxy-4-phenyl-butyl}-N-cyclopropylpyrrolidine-2(S)-carboxamide | 100 |

TABLE I-continued

| ENTRY NO. | COMPOUND | IC$_{50}$ (nM) |
|---|---|---|
| 8 | 4(R)-Benzyl-1-{3(S)-{{N-(benzyloxycarbonyl)asparaginyl}amino}-2(R)-hydroxy-4-phenylbutyl}-N-tert-butyl-pyrrolidine-2(S)-carboxamide | 48 |
| 9 | 4(S)-Benzyl-1-{3(S)-{{N-(benzyloxycarbonyl)asparaginyl}amino}-2(R)-hydroxy-4-phenylbutyl}-N-tert-butyl-pyrrolidine-2(S)-carboxamide | 780 |
| 10 | N-tert-butyl-1-{2(R)-hydroxy-4-phenyl-3(S)-{{N-(2-quinolinylcarbonyl)valyl}amino}butyl}-4(R)-(2-pyrimidinylthio)-pyrrolidine-2(S)-carboxamide | 4.7 |
| 11 | N-tert-butyl-1-{2(R)-hydroxy-4-phenyl-3(S)-{{N-(2-quinolinylcarbonyl)valyl}amino}butyl}-4(R)-{(3-pyridinylmethyl)-thio}pyrrolidine-2(S)-carboxamide | 12 |
| 12 | N-tert-butyl-1-{2(R)-hydroxy-4-phenyl-3(S)-{{N-(2-quinolinylcarbonyl)valyl}amino}butyl}-4(R)-{(2,6-dimethyl-4-pyrimidinyl)oxy}pyrrolidine-2(S)-carboxamide | 9.4 |
| 13 | N-tert-butyl-1-{3(S)-{{(2,6-dimethylphenoxy)acetyl}amino}-2(R)-hydroxy-4-phenylbutyl}-4(R)-(2-pyrimidinylthio)-pyrrolidine-2(S)-carboxamide | 4.6 |
| 14 | N-tert-butyl-1-{3(S)-{{(2,6-dimethylphenoxy)acetyl}amino}-2(R)-hydroxy-4-phenylbutyl}-4(R)-{(3-pyridinylmethyl)-thio}pyrrolidine-2(S)-carboxamide | 43 |

EXAMPLE 14

The following protocol, used for screening antiviral effects of the compounds of formula 1, is adapted from a plaque assay utilizing HTLV-I transformed cells, previously reported by Harada et al., supra. HTLV-I transformed cells are used because of the rapidity with which HIV will replicate in the cells.

1. The test compound is dissolved in dimethylsulfoxide to a concentration of 5 mg/mL. The resultant solution can be stored at 4° until use.

2. The resultant solution is diluted in RPMI 1640 (Gibco Laboratories, St. Lawrence, Mass., USA) to four times (4×) the final concentration which is to be tested. Once diluted in RPMI 1640, the solution is used in the cell culture assay within 4 h.

3. The 4×solution (50 μL) is added to triplicate wells of a 96 well flat bottomed microtiter plate. RPMI (50 μL) also is added to control wells.

4. C8166 cells (5×10$^4$) in 50 ML of HEPES-buffered RPMI 1640 (pH=7.2), 10% heat inactivated fetal calf serum (FCS), 12.5 μL/mL gentamicin (complete media) are added to all wells.

5. Fifty times TCID$_{50}$ of H9/HTLV-IIIB stock (stored in liquid nitrogen as cell culture supernatant in 50% FCS) in 100 μL of complete media is added to all wells. Infectious titer of virus stocks are as previously determined by end point dilution on C8166 cells. Titer of stocks are stable for 6–12 months when stored at −193°.

6. Microtiter plates are then placed on level shelves of a 37°, 5% CO$_2$ humidified incubator for 72 h.

7. Plates are then removed and centers of syncytia are counted in each well by low power phase contrast light microscopy. Each cluster of cells which shows evidence of any syncytia formation is counted as one center of syncytia. Control wells should have between 25 and 75 centers of syncytia per well.

8. Percent inhibition of syncytia formation is calculated by the formula:

$$\% \text{ inhibition} = 100 \times \frac{\left(\begin{array}{c}\text{\# syncytial centers}\\ \text{in control wells}\end{array}\right) - \left(\begin{array}{c}\text{\# syncytial centers in}\\ \text{test wells}\end{array}\right)}{\left(\begin{array}{c}\text{\# syncytial center in}\\ \text{control wells}\end{array}\right)}$$

The concentration of the test compound which causes a 50% inhibition of syncytia formation, i.e. the EC$_{50}$, is determined by using the technique of serial dilution of the working solution at step 3 and graphically plotting the observed percent inhibition of syncytia formation against the various concentrations of the test compound.

In the following Table II, assay results are listed for exemplified compounds of formula 1 from the plaque assay of this example.

TABLE II

| ENTRY NO. | COMPOUND | EC$_{50}$ (nM) |
|---|---|---|
| 1 | 4(R)-Benzyloxy-1-{3(S)-{{N-(benzyloxycarbonyl)valyl}-amino}-2(R)-hydroxy-4-phenylbutyl}-N-tert-butyl-pyrrolidine-2(S)-carboxamide | 600 |
| 2 | 4(R)-Benzyloxy-1-{3(S)-{{N-benzyloxycarbonyl)asparaginyl}amino}-2(R)-hydroxy-4-phenylbutyl}-N-tert-butyl-pyrrolidine-2(S)-carboxamide | 600 |
| 3 | 1-{3(S)-{{N-(benzyloxycarbonyl)valyl}amino}-2(R)-hydroxy-4-phenylbutyl}-N-tert-butyl-4(R)-(2-methylpropyloxy)pyrrolidine-2(S)-carboxamide | 3000 |
| 4 | 4(R)-Benzyloxy-1-{3(S)-{{N-(benzyloxycarbonyl)valyl}amino}-2(R)-hydroxy-4-phenylbutyl}-N-cyclopropylpyrrolidine-2(S)-carboxamide | 900 |
| 5 | 4(R)-Benzyl-1-{3(S)-{{N-(benzyloxycarbonyl)asparaginyl}amino}-2(R)-hydroxy-4-phenylbutyl}-N-tert-butyl-pyrrolidine-2(S)-carboxamide | 700 |
| 6 | 4(S)-Benzyl-1-{3(S)-{{N-(benzyloxycarbonyl)asparaginyl}amino}-2(R)-hydroxy-4-phenylbutyl}-N-tert-butyl-pyrrolidine-2(S)-carboxamide | 4000 |
| 7 | N-tert-butyl-1-{2(R)-hydroxy-4-phenyl-3(S)-{{N-(2-quinolinylcarbonyl)valyl}amino}butyl}-4(R)-(2-pyrimidinylthio)-pyrrolidine-2(S)-carboxamide | 250 |
| 8 | N-tert-butyl-1-{2(R)-hydroxy-4-phenyl-3(S)-{{N-(2-quinolinylcarbonyl)valyl}amino}butyl}-4(R)-{(3-pyridinylmethyl)-thio}pyrrolidine-2(S)-carboxamide | 480 |

TABLE II-continued

| ENTRY NO. | COMPOUND | EC$_{50}$ (nM) |
|---|---|---|
| 9 | N-tert-butyl-1-{2(R)-hydroxy-4-phenyl-3(S)-{{N-(2-quinolinylcarbonyl)valyl}amino}butyl}-4(R)-{(2,6-dimethyl-4-pyrimidinyl)oxy}pyrrolidine-2(S)-carboxamide | 390 |
| 10 | N-tert-butyl-1-{3(S)-{{(2,6-dimethylphenoxy)acetyl}amino}-2(R)-hydroxy-4-phenylbutyl}-4(R)-(2-pyrimidinylthio)-pyrrolidine-2(S)-carboxamide | 250 |

Other compounds of formula 1 are:

N-tert-butyl-1-{2(R)-hydroxy-4-phenyl-3(S)-{{N-(2-quinolinylcarbonyl)valyl}amino}butyl}-4(R)-(phenylsulfonyl)pyrrolidine-2(S)-carboxamide N-tert-butyl-1-{2(R)-hydroxy-4-phenyl-3 (S)-{{N-(2-quinolinylcarbonyl)valyl}amino}butyl}-4(R)-(2-pyridinylthio)pyrrolidine-2(S)-carboxamide N-tert-butyl-1-{2(R)-hydroxy-4-phenyl-3(S)-{{N-(2-quinolinylcarbonyl)valyl}amino}butyl}-4(R)-(4-pyridinylthio)pyrrolidine-2(S)-carboxamide N-tert-butyl-1-{2(R)-hydroxy-4-phenyl-3(S)-{{N-(2-quinolinylcarbonyl)valyl}amino}butyl}-4(R)-(4,6-dimethyl-2-pyrimidinylthio)pyrrolidine-2(S)-carboxamide N-tert-butyl-1-{2(R)-hydroxy-4-phenyl-3(S)-{{N-(2-pyridinylcarbonyl)valyl}amino}butyl}-4(R)-phenoxypyrrolidine-2(S)-carboxamide N-tert-butyl-1-{2(R)-hydroxy-4-phenyl-3(S)-{{N-(2-pyridinylcarbonyl)asparaginyl}amino}butyl}-4(R)-phenoxypyrrolidine-2(S)-carboxamide N-cyclopentyl-1-{2(R)-hydroxy-4-phenyl-3(S)-{{N-(2-quinolinylcarbonyl)leucyl}amino}butyl}-4(R)-(phenylsulfonyl)pyrrolidine-2(S)-carboxamide 1-{2(R)-hydroxy-4-phenyl-3(S)-{{N-(2-quinolinylcarbonyl)valyl}amino}butyl}-N-(1-methylethyl)-4(R)-(2-pyridinylthio)pyrrolidine-2(S)-carboxamide N-cyclopropyl-1-{2(R)-hydroxy-4-phenyl-3(S)-{{N-(2-quinolinylcarbonyl)asparaginyl}amino}butyl}-4(R)-(4-pyridinylthio)pyrrolidine-2(S)-carboxamide N-tert-butyl-1-{2(R)-hydroxy-4-phenyl-3(S)-{{N-(2-quinolinylcarbonyl)isoleucyl}amino}butyl}-4(R)-(2-pyrimidinylthio)pyrrolidine-2(S)-carboxamide N-tert-butyl-1-{2(R)-hydroxy-4-phenyl-3(S)-{{N-(2-naphthylcarbonyl)valyl}amino}butyl}-4(R)-(4,6-dimethyl-2-pyrimidinylthio ) pyrrolidine-2(S)-carboxamide N-tert-butyl-1-{2(R)-hydroxy-4-phenyl-3(S)-{{N-(2-pyridinylcarbonyl)isoleucyl}amino}butyl}-4(R)-phenoxypyrrolidine-2(S)-carboxamide N-tert-butyl-1-{2(R)-hydroxy-4-phenyl-3(S)-{{N-(2-pyridinylcarbonyl)asparaginyl}amino}butyl}-4(R)(phenylthio)pyrrolidine-2(S)-carboxamide

We claim:

1. A compound selected from the group consisting of:

4(S)-Benzyloxy-1-{3(S)-{{N-(benzyloxycarbonyl)valyl}amino}-2(R)-hydroxy-4-phenylbutyl}-N-tert-butylpyrrolidine-2(S)-carboxamide, 4(R)-Benzyloxy-1-{3(S)-{{N-(benzyloxycarbonyl)valyl}amino}-2(R)-hydroxy-4-phenylbutyl}-N-tert-butylpyrrolidine-2(S)-carboxamide, 4(R)-Benzyloxy-1-{3(S)-{{N-(benzyloxycarbonyl)asparaginyl}amino}-2(R)-hydroxy-4 -phenylbutyl}-N-tert-butylpyrrolidine-2(S)-carboxamide, 4(S)-Benzyloxy-1-{3(S)-{{N-(benzyloxycarbonyl)asparaginyl}amino}-2(R)-hydroxy-4 -phenylbutyl}-N-tert-butylpyrrolidine-2(S)-carboxamide, 4(R)-Benzyloxy-1-{3(S)-{{N-(benzyloxycarbonyl)valyl}amino}-2(R)-hydroxy-4-phenylbutyl}-N-cyclopropylpyrrolidine-2(S)-carboxamide, 4(R)-Benzyl-1-{3(S)-{{N-(benzyloxycarbonyl)asparaginyl}amino}-2(R)-hydroxy-4-phenylbutyl}-N-tert-butylpyrrolidine-2(S)-carboxamide, 4(S)-Benzyl-1-{3(S)-{{N-(benzyloxycarbonyl)asparaginyl}amino}-2(R)-hydroxy-4-phenylbutyl}-N-tert-butylpyrrolidine-2(S)-carboxamide, N-tert-butyl-1-{2(R)-hydroxy-4-phenyl-3(S)-{{N-(2-quinolinylcarbonyl)valyl}amino}butyl}-4(R)-(2-pyrimidinylthio)pyrrolidine-2(S)-carboxamide, N-tert-butyl-1-{2(R)-hydroxy-4-phenyl-3(S)-{{N-(2-quinolinylcarbonyl)valyl}amino}butyl}-4(R)-{(3-pyridinylmethyl)thio}pyrrolidine-2(S)-carboxamide, N-tert-butyl-1-{2(R)-hydroxy-4-phenyl-3(S)-{{N-(2-quinolinylcarbonyl)valyl}amino}butyl}-4(R)-{(2,6-dimethyl-4-pyrimidinyl)oxy}pyrrolidine-2(S)-carboxamide, N-tert-butyl-1-{3(S)-{{(2,6-dimethylphenoxy)acetyl}amino}-2(R)-hydroxy-4-phenylbutyl}-4(R)-(2-pyrimidinylthio)-pyrrolidine-2(S)-carboxamide, and N-tert-butyl-1-{3(S)-{{2,6-dimethylphenoxy)acetyl}amino}-2(R)-hydroxy-4-phenylbutyl}-4(R)-{(3-pyridinylmethyl)thio}pyrrolidine-2(S)-carboxamide.

2. A pharmaceutical composition comprising a compound as recited in claim 1, or a therapeutically acceptable salt thereof, and a pharmaceutically acceptable carrier.

3. A method for treating HIV infection in a human comprising administering thereto an effective amount of a compound as defined in claim 1, or a therapeutically acceptable salt thereof.

* * * * *